United States Patent [19]

Österberg et al.

[11] Patent Number: 5,919,908
[45] Date of Patent: Jul. 6, 1999

[54] PROTEIN FORMULATION COMPRISING COAGULATION FACTOR VIII OR FACTOR IX IN AN AQUEOUS SOLUTION

[75] Inventors: Thomas Österberg; Angelica Fatouros, both of Stockholm, Sweden

[73] Assignee: Pharmacia & Upjohn AB, Stockholm, Sweden

[21] Appl. No.: 08/913,263

[22] PCT Filed: Mar. 9, 1996

[86] PCT No.: PCT/SE96/00419

§ 371 Date: Nov. 26, 1997

§ 102(e) Date: Nov. 26, 1997

[87] PCT Pub. No.: WO96/30041

PCT Pub. Date: Oct. 3, 1996

[30] Foreign Application Priority Data

Mar. 31, 1995 [SE] Sweden .................................. 9501189

[51] Int. Cl.⁶ .......................... A61K 35/14; A61K 38/00
[52] U.S. Cl. .......................... 530/383; 530/380; 530/384; 530/414; 530/417; 530/427; 530/829; 530/830; 514/12; 514/21; 514/53; 514/834
[58] Field of Search ..................................... 530/383, 380, 530/384, 414, 417, 427, 829, 830; 514/12, 21, 53, 834

[56] References Cited

U.S. PATENT DOCUMENTS

| | | | |
|---|---|---|---|
| 4,297,344 | 10/1981 | Schwinn et al. | 530/381 |
| 4,447,416 | 5/1984 | Menache-Arouson et al. | 424/101 |
| 4,891,319 | 1/1990 | Roser | 435/188 |
| 5,328,694 | 7/1994 | Schwinn | 424/423 |
| 5,733,873 | 3/1998 | Osterberg et al. | 514/12 |

FOREIGN PATENT DOCUMENTS

| | | |
|---|---|---|
| 0556096 | 8/1983 | European Pat. Off. |
| 0556609 | 8/1983 | European Pat. Off. |
| 0117064 | 8/1984 | European Pat. Off. |
| 0197901 | 10/1986 | European Pat. Off. |
| WO 9109122 | 6/1991 | WIPO |
| WO 9118091 | 11/1991 | WIPO |
| WO 9417834 | 8/1994 | WIPO |
| WO 9426286 | 11/1994 | WIPO |
| WO94/26286 | 11/1994 | WIPO |
| WO 9507713 | 3/1995 | WIPO |

OTHER PUBLICATIONS

Goulian et al (1966), *Nature*, vol. 211, No. 5044, pp. 74–75.
Schwinn et al (1989), *Arzneim.–Forsch./Drug Res.*, 39(II), No. 10, pp. 1302–1305.
Andersson et al (1986), *Proc. Natl. Acad. Sci. USA*, vol. 83, pp. 2979–2983.
*Factor VIII Coagulations Sanguinis Humani Cryodesiccatus*(1994), pp. 275–1 to 275–4.
Wan et al (1974), *Journal of Pharmaceutical Sciences*, vol. 63, No. 1, pp. 136–137.
Wang et al., *Journal of Parenteral Science and Technology*, Technical Report No. 10, 1988 Supplement, vol. 42, No. 2S.

*Primary Examiner*—Cecilia J. Tsang
*Assistant Examiner*—Abdel A. Mohamed
*Attorney, Agent, or Firm*—Dinsmore & Shohl LLP

[57] ABSTRACT

A final drug product comprises a plasma protein selected from the group consisting of coagulation factor VIII and factor IX, in an aqueous solution. The concentration of oxygen in the solution is reduced and/or the solution contains an antioxidant. The solution further contains a carbohydrate in a concentration of at least 350 mg/ml. The protein activity after storage for at least 6 months at a temperature of from 0° C. to 40° C. is from 70% to 130% of its initial value. In a process for preparing the final drug product and a method for improving the long-term stability of coagulation factor VIII or factor IX in an aqueous solution, a carbohydrate is included in the solution in a concentration of at least 350 mg/ml and the solution is stored in its final container under an oxygen-reduced atmosphere or includes an antioxidant.

29 Claims, No Drawings

PROTEIN FORMULATION COMPRISING COAGULATION FACTOR VIII OR FACTOR IX IN AN AQUEOUS SOLUTION

FIELD OF THE INVENTION

The present invention relates to a final drug product of a plasma protein selected from the group consisting of coagulation factor VIII and factor IX, in an aqueous solution, wherein the concentration of oxygen in the solution is reduced and/or the solution contains an antioxidant, and wherein the solution further contains a carbohydrate in a concentration of at least 350 mg/ml. In this way, the protein activity can be essentially retained after storage for at least 6 months. The present invention also relates to a process for preparing the final drug product, and a method for improving the long-term stability of coagulation factor VIII and factor IX in an aqueous solution, wherein the solution contains a carbohydrate in a concentration of at least 350 mg/ml, and wherein the solution is stored in its final container under an oxygen-reduced atmosphere.

BACKGROUND OF THE INVENTION

The stability of proteins is generally a problem in pharmaceutical industry. It has often been solved by drying the protein in various drying processes, such as freeze-drying. The protein has thereafter been distributed and stored in dried form. The solution before drying or freeze-drying, the dried material and the re-constituted product should all be stable, to avoid a substantial loss of activity in the drying process, as well as during storage or handling. The freeze-drying process is a costly and time consuming process step, which reduces the yield of the product. It would therefore be a great advantage if this step could be avoided when preparing a commercial product. Furthermore, the patient necessarily has to reconstitute the dried protein in a solvent before use, which could be inconvenient for the patient.

Hemophilia is an inherited disease which has been known for centuries but it is only within the last four decades that it has been possible to differentiate between the various forms; hemophilia A and hemophilia B. Hemophilia A is the most frequent form. It affects only males with an incidence of one or two individuals per 10,000 live-born males. The disease is caused by strongly decreased level or absence of biologically active coagulation factor VIII (antihemophilic factor), which is a protein normally present in plasma. The clinical manifestation of hemophilia A is a strong bleeding tendency and before treatment with factor VIII concentrates was introduced, the mean age of the patients concerned was less than 20 years. Concentrates of factor VIII obtained from plasma have been available for about three decades. This has improved the situation for treatment of hemophilia patients considerably and offered them possibility of living a normal life.

A formulation with a low concentration of a protein such as factor VIII, will generally loose activity during purification, sterile manufacturing, in the package and during administration. This problem is usually solved by the addition of human serum albumin (HSA) which reduces the loss of the active protein considerably. HSA functions as a general stabilizer during purification, sterile manufacturing and freeze-drying (see review by Wang et al., J. of Parenteral Sci. and Tech. Vol 42, Number 2S, supplement. 1988). The use of HSA for stabilization of factor VIII is known and is currently used in all highly purified factor VIII products on the market. However, use of HSA is costly and it is desirable to avoid addition of HSA to a therapeutic protein manufactured by recombinant DNA technology. In addition, the use of HSA as a formulation excipient often limits the use of many of the most powerful and sensitive analytical methods for protein characterization.

Several solutions have been proposed for stabilizing various proteins without using HSA. For example, WO-A-94/26286 to Pharmacia proposes reducing the oxygen concentration as a means to improve the stability of factor VIII solutions ready for use. Furthermore, carbohydrates such as disaccharides or sugar alcohols, have been used previously for stabilizing solutions containing conventional factor VIII products with a low purity. Thus, patent specification WO-A-91/10439 to Octapharma discloses injectable solutions containing factor VIII or factor IX, comprising natural or synthetic disaccharides in a concentration of from 0.1 up to 0.9 mol/l.

Carbohydrates such as disaccharides or sugar alcohols, have been used previously also for stabilizing factor VIII compositions during heat treatment for inactivating viruses. Thus, patent specification EP-B-0 117 064 to Green Cross discloses the presence of at least 1,500 mg/ml of a sugar alcohol or a disaccharide stabilizer, preferably sorbitol or saccharose. The process can be carried out for 3 up to 24 hours at 30 to 80° C., or for 1 min at 90° C. The sugar alcohol or disaccharide are removed after the heat treatment, e.g. by ultrafiltration. Patent specification EP-A-0 018 561 to Behringwerke discloses the presence of an amino acid and 20 to 60% (w/w) of a monosaccharide, an oligosaccharide or a sugar alcohol. This corresponds to 500 to 1,500 mg/ml of saccharide or alcohol assuming the specific gravity of the solution to be 1. The process can be carried out for 1 min up to 48 hours, at 30 to 100° C. Patent specification WO-A-94/17834 to Octapharma discloses heat treating compositions containing a protein and a dialkylphosphate or trialkylphosphate for 5 up to 30 hours at 55 up to 67° C. to inactivate viruses devoid of lipid envelopes. The composition can further contain stabilizing agents, such as saccharose, sorbitol or short-chained neutral amino acids.

WO-A-87/00196 to Quadrant Bioresources discloses the use of trehalose for protecting proteins and other macromolecules from denaturation during drying at ambient temperature. The examples reveal that the compounds tested, mainly antibodies and enzymes, are not only stabilized during the drying procedure, but are also stabilized against long-term storage at relatively high ambient temperature. There is no information about either factor VIII or factor IX, nor about aqueous solutions with a reduced concentration of oxygen.

In WO-A-91/18091 to Quadrant Holdings Cambridge it is stated that sugars in general are of limited use for stabilizing biological substances or organic compounds. Specifically, it is stated that non-reducing sugars, such as sucrose, provide very inferior long-term stabilization. To overcome this problem, WO-A-91/18091 discloses the use of certain sugar or sugar derivatives which can be dried without crystallizing and are non-reducing polyhydroxy compounds capable of replicating the effect of trehalose. More particularly, the sugar or sugar derivatives are selected from (i) a non-reducing glycoside of a polyhydroxy compound selected from sugar alcohols and other straight chain polyalcohols, or (i) a non-reducing oligosaccharide selected from raffinose, stachyose and melezitose. There is no information about either factor VIII or factor IX, nor about aqueous solutions with a reduced concentration of oxygen.

It would facilitate the use and manufacture of plasma proteins if the protein could be formulated and distributed to the patient as a stable solution without the addition of albumin and with a prolonged storage life. Also for the patient such a solution would facilitate the handling of the final drug product. The patient could thus administer, e.g. inject, the content of the final drug product directly without reconstitution.

SUMMARY OF THE INVENTION

Factor VIII solutions are thus virus inactivated by heat treating the solutions containing various stabilizers for a period of time which is less than about two days. Techniques to stabilize proteins subjected to a high temperature for a short period of time, cannot, however, be directly transferred to stability in storage at a low or ambient temperature for several months or years. This is especially true since, in general, the saccharides or sugar alcohols added are removed, intentionally or inevitably, in the process steps following the heat treatment. Reference is here made to Schwinn et al, Arzneim.-Forsch/Drug Res., Vol. 39 (II), 10, p. 1302–1305 (1989). Also, the feasibility of the formulation in sterile manufacturing must be considered.

The inventors of the present invention have surprisingly found that the storage stability of aqueous solutions ready for use containing coagulation factor VIII or factor IX, can be dramatically improved by the presence of a high proportion of carbohydrates. It is also surprising that aqueous factor VIII solutions containing a high proportion of carbohydrates can be sterile filtered directly without an intermediate step to lower the concentration of the carbohydrates.

Thus, the present invention relates to a final drug product of a plasma protein selected from the group consisting of coagulation factor VIII and factor IX, in an aqueous solution, wherein the concentration of oxygen in the solution is reduced and/or the solution contains an antioxidant, and wherein the solution further contains a carbohydrate in a concentration of at least 350 mg/ml, for essentially retaining the protein activity after storage for at least 6 months.

The protein activity is retained to a higher degree when the concentration of the carbohydrate lies in the range of from 450 mg/ml up to saturation at the conditions prevailing in the final drug product. Suitably, the concentration of the carbohydrate lies in the range of from 550 mg/ml up to saturation at the conditions prevailing in the final drug product. Preferably, the concentration of the carbohydrate lies in the range of from 650 mg/ml up to saturation at the conditions prevailing in the final drug product. The saturation concentration for each carbohydrate is e.g. influenced by the temperature, ionic strength, pH, and other excipients if present.

The high concentration of carbohydrate in the plasma protein solution yields a final drug product with a markedly improved storage stability, compared to previously known plasma protein products. Thus, the final drug product of the present invention, is stored for at least 6 months with essentially retained protein activity. In the present invention, essentially retained activity relates to an activity in the range of from 70 up to 130% of the initial value, preferably in the range of from 80 up to 120% of the initial value. The latter range is consistent with the requirements of the test for potency for Freezedried Human Coagulation Factor VIII. Thus, in the European Pharmacopeia, 1994, p. 275, it is stated that the activity must be retained within the range of from 80 up to 120% of the labeled value. Suitably, the present final drug products are stored for at least 12 months, and preferably for at least 18 months, with essentially retained factor VIII activity. More preferably, the present final drug products are stored for at least 24 months.

The high concentration of carbohydrate in the plasma protein solution also allows for storage at a higher temperature than previously deemed possible to avoid a drop in protein activity. Thus, the present final drug product can be stored at a temperature in the range of from 0 up to 40° C. The present final drug product is suitably stored at a temperature in the range of from 2 up to 30° C., and preferably at a temperature in the range of from 4 up to 20° C. It is even quite possible to store the present final drug product during a long-term period at a temperature in the range of from 10 up to 25° C.

Final drug product relates to a stable, generally injectable aqueous solution in its final container. The final drug product thus comprises a stable aqueous solution ready for use. The final drug product is obtained after purification including one or more sterile filtering steps, and, optionally, one or more virus-inactivation steps. Suitable containers in the present invention are e.g. vials, syringes and injection devices.

DETAILED DESCRIPTION OF THE INVENTION

The carbohydrate of the present invention can be selected from any pharmaceutically acceptable natural or synthetic carbohydrate, such as a monosaccharide, disaccharide, oligosaccharide, polysaccharide or sugar alcohol or mixtures thereof. Examples of naturally occurring disaccharides are sucrose (saccharose), trehalose, maltose, cellobiose and lactose. Examples of polysaccharides are starch and derivatives thereof, and cellulose and derivatives thereof. Sugar alcohols contain hydroxy groups, and are obtained by reduction of various monosaccharides. For example, sorbitol is obtained by reduction of glucose, and mannitol is obtained from mannose.

The carbohydrate of the present invention is suitably selected from the group consisting of natural or synthetic disaccharides, and sugar alcohols, and mixtures thereof. More suitably, the carbohydrate is non-reducing, since this reduces the risk for degradation of the coagulation factor VIII and factor IX molecules. Examples of non-reducing carbohydrates are sucrose, trehalose, mannitol, sorbitol, galactitol and xylitol. Preferably, the non-reducing carbohydrate is sucrose or sorbitol, or mixtures thereof. More preferably, the carbohydrate is sucrose.

The invention also relates to a process for preparing the final drug product, wherein the plasma protein is mixed with an aqueous solution, or wherein the plasma protein is eluted from the last purifying step with an aqueous buffer solution. Thereafter, a carbohydrate is added to the obtained aqueous solution containing the plasma protein. The carbohydrate is added such that the concentration of carbohydrate is at least 350 mg/ml in the final drug product. Suitably, the concentration of carbohydrate of the aqueous solution containing the plasma protein lies in the range of from 450 mg/ml up to saturation at the conditions prevailing in the final drug product, preferably in the range of from 550 mg/ml up to saturation, and more preferably in the range of from 650 mg/ml up to saturation.

The aqueous solution containing the plasma protein and a carbohydrate is then sterile filtered. Thereafter, the sterile plasma protein solution containing carbohydrate is dispensed in its final container whereupon the oxygen concentration of the plasma protein solution is reduced. The two steps following the sterile filtration may also be carried out in the reverse order, i.e. the oxygen concentration of the sterile plasma protein solution containing carbohydrate is first reduced whereupon the plasma protein solution is dispensed in its final container.

In one embodiment, the concentration of oxygen is reduced either by subjecting the aqueous solution to an inert gas atmosphere, by reducing the pressure, or by first reducing the pressure and thereafter introducing an inert gas. The latter process is preferably repeated in several cycles. By this method, the resulting concentration of oxygen in the solution will be substantially lower than would be the case if the surrounding atmosphere consisted of air. Thus, by this method the oxygen concentration in the solution can be reduced to a low level, without a substantial loss in plasma protein activity. The oxygen content in the solution can be below 200 ppm, suitably below 50 ppm, preferably below 10 ppm and more preferably below 2 ppm. The oxygen content in the container used can be reduced and maintained at a low level in the same way, preferably by subjecting the container to an inert gas atmosphere.

The aqueous solution containing a plasma protein and a carbohydrate is suitably stored under an inert gas such as nitrogen, argon or helium, to essentially maintain the low content of oxygen. The inert gas is preferably a non-noble inert gas, and more preferably nitrogen.

The low content of oxygen can also be essentially maintained by adding an antioxidant to the aqueous solution. Thus, in another embodiment, an antioxidant is added before the sterile filtering step and the concentration of oxygen is reduced either by subjecting the aqueous solution to an inert gas atmosphere, by reducing the pressure, or by first reducing the pressure and thereafter introducing an inert gas, preferably repeated in several cycles.

In yet another, and less preferred, embodiment, an antioxidant is added to the aqueous solution before the sterile filtering step, without reducing the oxygen concentration by other means.

The antioxidant can be selected from glutathione, acetylcysteine, methionine, tocopherol, butyl hydroxy toluene, butyl hydroxy anisole or phenolic compounds. Preferably, the antioxidant is at least one compound selected from the group consisting of glutathione, acetylcysteine and methionine.

The concentration and total amount of the antioxidant depends on the compound used. Therefore, no concentration or amount can generally be given. It is, however, important that the total amount of antioxidant, if used, is a pharmaceutically acceptable amount.

Complexing agents, such as EDTA and citric acid, can also be present in small concentrations for stabilizing the formulation, if they exhibit a stronger affinity for destabilizing metal ions than for the metal ions associating the chains of e.g. factor VIII.

The invention also relates to a method for improving the long-term stability of plasma proteins in an aqueous solution, wherein the solution further contains a carbohydrate in a concentration of at least 350 mg/ml, and that the solution is stored in its final container under an oxygen-reduced atmosphere, preferably under an inert gas atmosphere. Suitably, the plasma protein is factor VIII and the concentration of carbohydrate of the aqueous solution stored in its final container lies in the range of from 450 mg/ml up to saturation at the conditions prevailing in the final drug product, preferably in the range of from 550 mg/ml up to saturation, and more preferably in the range of from 650 mg/ml up to saturation.

While the invention is applicable mainly to plasma proteins selected from the group consisting of coagulation factor VIII and factor IX, it may be used to advantage also for other plasma proteins, such as antithrombin III. The invention will in the following be described in more detail with reference to factor VIII.

The pH of the solution is suitably in the range of from 6.0 up to 8.0, preferably from 6.5 up to 7.5.

A non-ionic surfactant is preferably present in the solution. The non-ionic surfactant, if present, is preferably chosen from block co-polymers such as a poloxamer or polyoxyethylene sorbitan fatty acid ester, such as polysorbate 20 or polysorbate 80.

The non-ionic surfactant should, if present, be used in a concentration above the critical micelle concentration (CMC). See Wan and Lee, Journal of Pharm Sci, 63, p. 136–137, 1974. The polyoxyethylene sorbitan fatty acid ester is thus preferably used in a concentration of at least 0.01 mg/ml.

The aqueous solution can further contain sodium or potassium chloride, suitably in a concentration of more than 0.1M, preferably more than 0.25M.

The aqueous solution suitably contains a buffering agent, in a concentration of more than 1 mM, preferably 10 to 95 mM. The buffering agent is preferably an amino acid selected from the group consisting of L-histidine, lysine and arginine, or mixtures thereof. More preferably, the buffering agent is L-histidine.

The final drug product preferably comprises an aqueous solution containing i) 10–50,000 IU/ml of recombinant coagulation factor VIII ii) at least 0.01 mg/ml of a polyoxyethylene sorbitan fatty acid ester iii) sodium chloride, suitably in a concentration of more than 0.1M, and preferably more than 0.25M iv) calcium salt, such as calcium chloride or calcium gluconate, preferably in a concentration of more than 0.5 mM.

v) a buffering agent, such as L-histidine, in a concentration of more than 1 mM vi) a disaccharide or a sugar alcohol, preferably sucrose or sorbitol, in a concentration of at least 350 mg/ml.

Factor VIII concentrates derived from human plasma contain several fragmented fully active factor VIII forms as described by Andersson et al, Proc. Natl. Acad. Sci. USA, 83, p. 2979–83 (May 1986). The smallest active form has a molecular mass of 170 kDa and consists of two chains of 90 kDa and 80 kDa held together by a metal ion bridge. Reference is here made to EP-A-0 197 901.

Pharmacia AB of Stockholm, Sweden, has developed a recombinant factor VIII product which corresponds to the 170 kDa plasma factor VIII form in therapeutic factor VIII concentrates. The truncated recombinant factor VIII molecule is termed r-VIII SQ and is produced by Chinese Hamster Ovary (CHO) cells in a cell culture process in serum-free medium. The specific activity of r-VIII SQ is about 15,000 IU VIII:C per mg of total protein. The structure and biochemistry of r-VIII SQ have been described in WO-A-91/09122 assigned to Pharmacia AB.

In the present invention, factor VIII can be either plasma factor VIII or recombinant factor VIII. When factor VIII is recombinant it can be full-length factor VIII, or preferably, a deletion derivative of full-ength factor VIII. More preferably, the deletion derivative is recombinant factor VIII SQ (r-VIII SQ). In this context, a deletion derivative is defined as a coagulation factor VIII, in which the whole or a part of the β-domain is missing.

The association of the heavy and light chains of factor VIII, is dependent on the presence of calcium (or other divalent metal ions). Here calcium was added as calcium chloride ($CaCl_2$), but other salts such as calcium gluconate, calcium glubionate or calcium gluceptate can also be used, preferably in a concentration of more than 0.5 mM.

The present invention can be used advantageously for a wide variety of factor VIII products. Thus, the present invention can be used to further stabilize plasma factor VIII which is already stabilized by association with its carrier protein, the von Willebrand factor (vWf). The advantage of the present invention becomes, however, more pronounced with highly purified factor VIII products, since these products are more unstable than less purified products containing e.g. the vWf. Thus, factor VIII products containing small amounts of the vWf or no vWf at all, are much more liable to degradation. Therefore, the present invention is suitably used with factor VIII products exhibiting a ratio of factor VIII:C (IU) to vWf:Ag (IU) of at least 2:1, more suitably of at least 10:1 and preferably of at least 100:1. More preferably, the factor VIII product of the present invention contains no vWf.

The specific factor VIII activity in the final drug product of the present invention is suitably at least 1,000 IU/mg of total protein, and more suitably at least 3,000 IU/mg of total protein. The specific factor VIII activity in the final drug product of the present invention is preferably at least 5,000 IU/mg of total protein, and more preferably at least 10,000 IU/mg of total protein.

The factor VIII activity in the final drug product can be in the range of from 10 up to 50,000 IU/ml, suitably from 50 up to 25,000 IU/ml, and preferably from 100 up to 10,000 IU/ml.

The present invention is advantageously used for final drug products of factor VIII and factor IX which have been stabilized without addition of albumin.

The following Examples are intended to further illustrate the invention by showing stability data for aqueous solutions containing various carbohydrates, without limiting the scope of protection.

EXPERIMENTAL

Preparation of recombinant factor VIII SQ

The preparation of recombinant factor VIII SQ (r-VIII SQ) was essentially performed as described in patent WO-A-91/09122, Examples 1–3. A DHFR deficient CHO celline (DG44N.Y.) was electroporated with an expression vector containing the r-VIII SQ gene and an expression vector containing the dihydrofolate-reductase gene. Following selection on selective media surviving colonies were amplified through growth in stepwise increasing amounts of methotrexate. Supernatant from the resulting colonies were individually screened for factor VIII activity. A production clone was chosen and this was subsequently adapted to serum-free suspension growth in a defined medium and finally a large scale fermentation process was developed. Supernatant is collected after certain time periods and further purified as described below.

The clarified conditioned medium was pH adjusted and applied to a S-Sepharose FF column. After washing, factor VIII was eluted with a salt buffer containing 5 mM $CaCl_2$.

Immunoadsorption was carried out on an immunoaffinity resin where the ligand was a monoclonal antibody (8A4) directed towards the heavy chain of Factor VIII. Before loading to the column the S-eluate was treated with 0.3% TNBP and 1% Octoxynol 9. The column was equilibrated, washed and factor VIII was eluted with a buffer containing 0.05M $CaCl_2$ and 50% ethylene glycol.

The mAb-eluate was loaded on a Q-Sepharose FF column, equilibrated with the elution buffer in the immunoaffinity step. After washing, factor VIII was eluted with 0.05M L-histidine, 4 mM $CaCl_2$, 0.6M NaCl, pH 6.8.

The Q-eluate was applied to a gel filtration column (Superdex 200 p.g.). Equilibration and elution was carried out with a formulation buffer containing L-Histidine, sodium chloride, calcium chloride and polysorbate 80 (see example 1 below), giving the composition according to the examples below.

Bulk material of r-VIII SQ was received from the final purification step. The activity of factor VIII and the concentration of the inactive components were adjusted by diluting with an appropriate buffer containing a carbohydrate. The solution was then sterile filtered (0.22 $\mu$m) and dispensed and deoxygenated by subjecting the solution to reduced pressure and thereafter introducing the inert gas in several cycles.

The activity of coagulation factor VIII (factor VIII:C) was assessed by a chromogenic substrate assay (Coatest Factor VIII, Chromogenix AB, Mölndal, Sweden). Activated factor X (Xa) is generated via the intrinsic pathway where factor VIII acts as co-factor. Factor Xa is then determined by the use of a synthetic chromogenic substrate, S-2222 in the presence of a thrombin inhibitor I-2581 to prevent hydrolysis of the substrate by thrombin. The reaction is stopped with acid, and the VIII:C, which is proportional to the release of pNA (para-nitroaniline), is determined photometrically at 450 nm against a reagent blank. The unit of factor VIII:C is expressed in international units (IU) as defined by the current International Concentrate Standard (IS) established by WHO. The relative standard deviation (RSD) of the method is 7%.

Example 1

Recombinant factor VIII (r-VIII SQ) was prepared according to the method described under Experimental. The factor VIII used in the Examples is highly purified, i.e. has a specific activity of more than 5,000 IU/mg of total protein, and is stabilized without the addition of albumin.

All of the compositions in this Example contained:

r-VIII SQ, IU/ml 125
L-Histidine, mg/ml 3
Sodium chloride, mg/ml 18
Calcium chloride, mM 3.4
Polysorbate 80, mg/ml 0.2

The dispensed volume in the vials was 1 ml, the headspace contained nitrogen and the pH was about 7.

The stabilizers used in the storage tests of Example 1, were of Ph. Eur. quality.

TABLE I

The aqueous factor VIII compositions used in the storage tests of Example 1

| | Carbohydrate concentration, mg/ml | | |
|---|---|---|---|
| Designation | Sucrose | Sorbitol | Mannitol |
| 1 (control) | — | — | — |
| 2 | 10 | — | — |
| 3 | 300 | — | — |
| 4 | 600 | — | — |
| 5 | — | 10 | — |
| 6 | — | 300 | — |
| 7 | — | 600 | — |
| 8 | — | — | 10 |
| 9 | — | — | 150* |

*Due to limited solubility at the prevailing conditions

TABLE II

Factor VIII activity initially (before storage)

| | Factor VIII activity, IU/ml | | |
|---|---|---|---|
| Designation | Test 1 | Test 2 | Mean value |
| 1 (control) | 122 | 120 | 121 |
| 2 | 119 | 109 | 114 |
| 3 | 116 | 109 | 113 |
| 4 | 118 | 108 | 113 |
| 5 | 107 | 100 | 104 |
| 6 | 110 | 112 | 111 |
| 7 | 39 | 40 | 40 |
| 8 | 121 | 117 | 119 |
| 9 | 118 | 112 | 115 |

TABLE III

Factor VIII activity after one month storage at 25 and 37° C., respectively
The percentage is calculated from the mean initial activity for each composition

| | Factor VIII activity | | | |
|---|---|---|---|---|
| | 25° C. | | 37° C. | |
| Designation | IU/ml | % | IU/ml | % |
| 1 (control) | 106 | 88 | 80 | 66 |
| 2 | 107 | 94 | 84 | 74 |
| 3 | 109 | 96 | 91 | 81 |
| 4 | 116 | 103 | 98 | 87 |
| 5 | 104 | 100 | 82 | 79 |
| 6 | 111 | 100 | 87 | 78 |
| 7 | 36 | 90 | 31 | 78 |
| 8 | 100 | 84 | 78 | 66 |
| 9 | 112 | 97 | 91 | 79 |

TABLE IV

Factor VIII activity after two month storage at 37° C.
The percentage is calculated from the mean initial activity for each composition

| | Factor VIII activity 37° C. | |
|---|---|---|
| Designation | IU/ml | % |
| 1 (control) | 52 | 43 |
| 2 | 53 | 46 |
| 3 | 64 | 57 |
| 4 | 81 | 72 |
| 5 | 52 | 50 |
| 6 | 63 | 57 |
| 7 | 22 | 55 |
| 8 | 53 | 45 |
| 9 | 64 | 56 |

TABLE V

Factor VIII activity after three months storage at 25° C.
The percentage is calculated from the mean initial activity for each composition

| | Factor VIII activity 25° C. | |
|---|---|---|
| Designation | IU/ml | % |
| 1 (control) | 79 | 65 |
| 2 | 86 | 75 |
| 3 | 98 | 87 |
| 4 | 121 | 107 |
| 5 | 80 | 77 |
| 6 | 102 | 92 |
| 7 | 35 | 88 |
| 8 | 87 | 73 |
| 9 | 94 | 82 |

TABLE VI

Factor VIII activity after six months storage at 7 and 25° C., respectively.
Mean of two samples per composition at 7° C.
The percentage is calculated from the mean initial activity for each composition

| | Factor VIII activity | | | |
|---|---|---|---|---|
| | 7° C. | | 25° C. | |
| Designation | IU/ml | % | IU/ml | % |
| 1 (control) | 76 | 63 | 55 | 45 |
| 2 | 79 | 69 | 60 | 53 |
| 3 | 109 | 96 | 78 | 69 |
| 4 | 124 | 110 | 103 | 91 |
| 5 | 82 | 79 | 57 | 55 |
| 6 | 112 | 101 | 78 | 70 |
| 7 | 41 | 103 | 29 | 73 |
| 8 | 82 | 69 | 64 | 54 |
| 9 | 100 | 87 | 71 | 62 |

TABLE VII

Factor VIII activity after nine months storage at 7 and 25° C., respectively.
The percentage is calculated from the mean initial activity for each composition

| | Factor VIII activity | | | |
|---|---|---|---|---|
| | 7° C. | | 25° C. | |
| Designation | IU/ml | % | IU/ml | % |
| 1 (control) | 70 | 58 | 44 | 36 |
| 2 | 67 | 59 | 46 | 40 |
| 3 | 105 | 93 | 57 | 50 |
| 4 | 124 | 110 | 85 | 75 |
| 5 | 78 | 75 | 50 | 48 |
| 6 | 102 | 92 | 59 | 53 |
| 7 | 38 | 95 | 23 | 58 |
| 8 | 71 | 60 | 48 | 40 |
| 9 | 89 | 77 | 53 | 46 |

TABLE VIII

Factor VIII activity after twelve months storage at 7 and 25° C., respectively.
Mean of two samples per composition at 7° C.
The percentage is calculated from the mean initial activity for each composition

| | Factor VIII activity | | | |
|---|---|---|---|---|
| | 7° C. | | 25° C. | |
| Designation | IU/ml | % | IU/ml | % |
| 1 (control) | 58 | 48 | 29 | 24 |
| 2 | 61 | 54 | 36 | 32 |
| 3 | 101 | 89 | 52 | 46 |
| 4 | 128 | 113 | 80 | 71 |
| 5 | 65 | 63 | 37 | 36 |
| 6 | 106 | 95 | 48 | 43 |
| 7 | 40 | 100 | 20 | 50 |
| 8 | 66 | 55 | 33 | 28 |
| 9 | 85 | 74 | 40 | 35 |

TABLE IX

Factor VIII activity after eighteen months storage at 7° C.
The percentage is calculated from the mean initial activity for each composition

| | Factor VIII activity 7° C. | |
|---|---|---|
| Designation | IU/ml | % |
| 1 (control) | 50 | 41 |
| 2 | 56 | 49 |
| 3 | 95 | 84 |
| 4 | 105 | 93 |
| 5 | 57 | 55 |
| 6 | 96 | 86 |
| 7 | 34 | 85 |
| 8 | 58 | 49 |
| 9 | 75 | 65 |

Example 2

Recombinant factor VIII (r-VIII SQ) was prepared according to the method described under Experimental. The factor VIII used in the Examples is highly purified, i.e. has a specific activity of more than 5,000 IU/mg of total protein, and is stabilized without the addition of albumin.

All of the compositions in this Example contained:

r-VIII SQ, IU/ml 500
L-Histidine, mg/ml 3
Sodium chloride, mg/ml 18
Calcium chloride, mM 3.4
Polysorbate 80, mg/ml 0.2

The dispensed volume in the vials was 1 ml.
The stabilizers used in the storage tests of Example 2, were of Ph. Eur. quality.

TABLE X

The aqueous factor VIII compositions used in the storage tests of Example 2

| Designation | Sucrose mg/ml | pH | Gas in headspace |
|---|---|---|---|
| 1 | 300 | 7 | Nitrogen |
| 2 | 400 | 7 | Nitrogen |
| 3 | 500 | 7 | Nitrogen |
| 4 | 600 | 7 | Nitrogen |
| 5 | 600 | 6.5 | Nitrogen |
| 6 | 600 | 7.5 | Nitrogen |
| 7 | 600 | 8 | Nitrogen |
| 8 | 600 | 7 | Air |

TABLE XI

Factor VIII activity initially (before storage)

| | Factor VIII activity, IU/ml | | |
|---|---|---|---|
| Designation | Test 1 | Test 2 | Mean value |
| 1 | 582 | 529 | 556 |
| 2 | 598 | 504 | 551 |
| 3 | 574 | 512 | 543 |
| 4 | 500 | 507 | 504 |
| 5 | 336 | 293 | 315 |
| 6 | 443 | 413 | 428 |
| 7 | 289 | 319 | 304 |

TABLE XI-continued

Factor VIII activity initially (before storage)

| Designation | Factor VIII activity, IU/ml | | |
|---|---|---|---|
| | Test 1 | Test 2 | Mean value |
| 8 | 478 | 484 | 481 |

TABLE XII

Factor VIII activity after one month storage at 37° C.
The percentage is calculated from the mean initial activity for each composition

| | Factor VIII activity 37° C. | |
|---|---|---|
| Designation | IU/ml | % |
| 1 | 383 | 69 |
| 2 | 399 | 72 |
| 3 | 400 | 74 |
| 4 | 428 | 85 |
| 5 | 256 | 81 |
| 6 | 353 | 82 |
| 7 | 246 | 81 |
| 8 | 73 | 15 |

TABLE XIII

Factor VIII activity after two months storage at 25 and 37° C., respectively
The percentage is calculated from the mean initial activity for each composition

| | Factor VIII activity | | | |
|---|---|---|---|---|
| | 25° C. | | 37° C. | |
| Designation | IU/ml | % | IU/ml | % |
| 1 | 368 | 66 | 251 | 45 |
| 2 | 429 | 78 | 295 | 54 |
| 3 | 410 | 76 | 289 | 53 |
| 4 | 445 | 88 | 330 | 65 |
| 5 | 288 | 91 | 213 | 68 |
| 6 | 422 | 99 | 288 | 67 |
| 7 | 268 | 88 | 183 | 60 |
| 8 | — | — | 10 | 2 |

TABLE XIV

Factor VIII activity after three months storage at 25 and 37° C., respectively
The percentage is calculated from the mean initial activity for each composition

| | Factor VIII activity | | | |
|---|---|---|---|---|
| | 25° C. | | 37° C. | |
| Designation | IU/ml | % | IU/ml | % |
| 1 | 352 | 63 | 179 | 32 |
| 2 | 407 | 74 | 204 | 37 |
| 3 | 376 | 69 | 205 | 38 |
| 4 | 432 | 86 | 259 | 51 |
| 5 | 290 | 92 | 186 | 59 |
| 6 | 389 | 91 | 228 | 53 |
| 7 | 254 | 84 | 124 | 41 |
| 8 | — | — | 3 | 1 |

TABLE XV

Factor VIII activity after nine months storage at 7 and 25° C., respectively
The percentage is calculated from the mean initial activity for each composition

| | Factor VIII activity | | | |
|---|---|---|---|---|
| | 7° C. | | 25° C. | |
| Designation | IU/ml | % | IU/ml | % |
| 1 | 372 | 67 | 173 | 31 |
| 2 | 434 | 79 | 242 | 44 |
| 3 | 404 | 74 | 255 | 47 |
| 4 | 458 | 91 | 348 | 69 |
| 5 | 274 | 87 | 205 | 65 |
| 6 | 368 | 86 | 261 | 61 |
| 7 | 228 | 75 | 130 | 43 |
| 8 | 190 | 40 | — | — |

We claim:

1. A final drug product of coagulation factor VIII in an aqueous solution, wherein the solution comprises at least one of (i) a reduced concentration of oxygen in the aqueous solution and (ii) an antioxidant, wherein the aqueous solution further comprises a carbohydrate in a concentration of at least 350 mg/ml, and wherein the final drug product has a factor VIII activity of from 70% to 130% of its initial value after storage for at least 6 months at a temperature of 0° C. to 40° C.

2. The final drug product according to claim 1, in which the antioxidant is a compound selected from the group consisting of glutathione, acetylcysteine and methionine, and mixtures thereof.

3. The final drug product according to claim 1, wherein the factor VIII activity is from 50 to 25,000 IU/ml.

4. The final drug product according to claim 1, wherein the factor VIII activity is at least 1,000 IU/mg.

5. The final drug product according to claim 1 wherein the factor VIII is free of the von Willebrand factor.

6. The final drug product according to claim 1, wherein the concentration of the carbohydrate is from 450 mg/ml up to saturation at the conditions prevailing in the final drug product.

7. The final drug product according to claim 1, wherein the concentration of the carbohydrate is from 550 mg/ml up to saturation at the conditions prevailing in the final drug product.

8. The final drug product according to claim 1, which further comprises an inert gas.

9. The final drug product according to claim 8, in which the inert gas is nitrogen.

10. The final drug product according to claim 1, wherein the carbohydrate is selected from the group consisting of non-reducing disaccharides, non-reducing sugar alcohols, and mixtures thereof.

11. The final drug product according to claim 10, wherein the non-reducing disaccharide is sucrose.

12. The final drug product according to claims 10, wherein the sugar alcohol is sorbitol.

13. The final drug product according to claim 1, wherein the factor VIII activity is from 80% to 120% of the initial value after storage.

14. The final drug product according to claim 13, wherein the factor VIII activity is from 80% to 120% of the initial value after storage for at least 12 months.

15. The final drug product according to claim 14, wherein the factor VIII activity is from 80% to 120% of the initial value after storage for at least 18 months.

16. The final drug product according to claim 1, wherein the factor VIII is a recombinant factor VIII selected from the group consisting of full-length factor VIII and deletion derivatives of full-length factor VIII.

17. Method for treatment of hemophilia A by administration of a therapeutically effective amount of recombinant factor VIII contained in a final drug product according to claim 16.

18. A method for improving the long-term stability of a plasma protein selected from the group consisting of coagulation factor VIII and factor IX, in an aqueous solution, comprising including in the aqueous solution a carbohydrate in a concentration of at least 350 mg/ml, and storing the aqueous solution containing the carbohydrate in its final container under an oxygen-reduced atmosphere.

19. The method according to claim 18, wherein the plasma protein is factor VIII, the aqueous solution comprises a carbohydrate in a concentration of at least 450 mg/ml, and the aqueous solution is stored in its final container under an inert gas atmosphere.

20. A final drug product of a plasma protein selected from the group consisting of coagulation factor VIII and factor IX, in an aqueous solution, wherein the solution comprises at least one of (i) a reduced concentration of oxygen in the aqueous solution, and (ii) an antioxidant, wherein the aqueous solution further comprises a carbohydrate in a concentration of at least 350 mg/ml, and wherein the final drug product has a plasma protein activity of from 70% to 130% of its initial value after storage for at least 6 months at a temperature of from 0° C. to 40° C.

21. A process for preparing the final drug product according to claim 20, comprising mixing a plasma protein with an aqueous solution, adding a carbohydrate to the aqueous solution wherein the concentration of the carbohydrate in the aqueous solution is at least 350 mg/ml, sterile filtering the aqueous solution, and subsequently, in arbitrary order, dispensing the aqueous solution in its final container, and reducing the oxygen concentration of the aqueous solution.

22. The Process for preparing the final drug product according to claim 21, wherein the concentration of carbohydrate in the aqueous solution is from 450 mg/ml up to saturation at the conditions prevailing in the final drug product.

23. The process for preparing the final drug product according to claim 22, wherein the concentration of carbohydrate in the aqueous solution is from 550 mg/ml to saturation at the conditions prevailing in the final drug product.

24. A process for preparing the final drug product according to claim 20, comprising eluting a plasma protein from a last purifying step with an aqueous buffer solution, adding a carbohydrate to the aqueous solution wherein the concentration of carbohydrate in the aqueous solution is at least 350 mg/ml, sterile filtering the aqueous solution, and subsequently, in arbitrary order, dispensing the aqueous solution in its final container, and reducing the concentration of the aqueous solution.

25. The Process for preparing the final drug product according to claim 24, wherein the concentration of carbohydrate in the aqueous solution is from 450 mg/ml up to saturation at the conditions prevailing in the final drug product.

26. The process for preparing the final drug product according to claim 25, wherein the concentration of carbohydrate in the aqueous solution is from 550 mg/ml to saturation at the conditions prevailing in the final drug product.

27. A process for preparing the final drug product according to claim 20, comprising mixing a plasma protein with an aqueous solution, adding a carbohydrate to the aqueous solution wherein the concentration of carbohydrate in the aqueous solution is at least 350 mg/ml, adding an antioxidant to the aqueous solution, sterile filtering the aqueous solution, and subsequently dispensing the aqueous solution in its final container.

28. The Process for preparing the final drug product according to claim 27, wherein the concentration of carbohydrate in the aqueous solution is from 450 mg/ml up to saturation at the conditions prevailing in the final drug product.

29. The process for preparing the final drug product according to claim 28, wherein the concentration of carbohydrate in the aqueous solution is from 550 mg/ml to saturation at the conditions prevailing in the final drug product.

* * * * *

UNITED STATES PATENT AND TRADEMARK OFFICE
CERTIFICATE OF CORRECTION

PATENT NO. : 5,919,908
DATED : July 6, 1999
INVENTOR(S) : Thomas Österberg et al It is certified that error appears in the above-identified patent and that said Letters Patent is hereby corrected as shown below:

On the cover page, item [22], change the PCT Filed date to --March 29, 1996--.

Column 14, claim 1, line 2, change "wherein the solution comprises" to --wherein the aqueous solution comprises--.

Column 15, claim 20, line 3, change "wherein the solution comprises" to --wherein the aqueous solution comprises--.

Column 15, claim 22, line 1, change "The Process" to --The process--.

Column 16, claim 24, line 8, change "the concentration" to --the oxygen concentration--.

Column 16, claim 25, line 1, change "The Process" to --The process--; line 3, delete "up".

Column 16, claim 28, line 1, change "The Process" to --The process--; line 3, delete "up".

Signed and Sealed this

Fourth Day of January, 2000

Attest:

Attesting Officer

*Acting Commissioner of Patents and Trademarks*